United States Patent [19]

Krüeger et al.

[11] 4,094,782

[45] June 13, 1978

[54] N-ACYL-1-AMINO ALKANE-1,1-DIPHOSPHONIC ACID COMPOUNDS AND COMPOSITIONS FOR AND METHOD OF USING SAME

[75] Inventors: Friedrich Krüeger, Edingen; Walter Michel, Ilvesheim, both of Germany

[73] Assignee: Joh. A. Benckiser, Ludwigshafen am Rhein, Germany

[21] Appl. No.: 760,368

[22] Filed: Jan. 18, 1977

Related U.S. Application Data

[62] Division of Ser. No. 667,286, Apr. 15, 1976, Pat. No. 4,029,697.

[30] Foreign Application Priority Data

Apr. 30, 1975 Germany .............................. 2519264
Jul. 5, 1975 Germany .............................. 2530139

[51] Int. Cl.$^2$ .............................................. C02B 5/06
[52] U.S. Cl. ...................................... 210/58; 252/180
[58] Field of Search ............ 260/502.5, 429 J, 439 R; 210/58; 252/180

[56] References Cited

U.S. PATENT DOCUMENTS

| | | | |
|---|---|---|---|
| 2,993,067 | 7/1961 | Magerlein et al. | 260/502.5 |
| 3,173,944 | 3/1965 | Kroll et al. | 260/502.5 |
| 3,853,530 | 12/1974 | Franz | 260/502.5 |
| 3,919,297 | 11/1975 | Krüeger et al. | 260/502.5 |
| 3,957,160 | 5/1976 | Ploger et al. | 210/58 |

FOREIGN PATENT DOCUMENTS

| | | | |
|---|---|---|---|
| 339,925 | 9/1959 | Switzerland | 260/502.5 |
| 866,409 | 4/1961 | United Kingdom | 260/502.2 |

*Primary Examiner*—Thomas G. Wyse
*Attorney, Agent, or Firm*—Bacon & Thomas

[57] ABSTRACT

N-acyl-1-amino alkane-1,1-diphosphonic acids or their alkali metal salts are highly effective scale and deposit formation preventing, metal ion complexing, sequestering, and anti-corrosive agents which can be used with great advantage in washing and cleaning fluids and detergent preparations. Such N-acyl-1-amino alkane-1,1-diphosphonic acids are prepared, for instance, by acylating the corresponding 1-amino alkane-1,1-diphosphonic acids or by hydrolyzing the corresponding (1,1-diphosphono alkane) acylamidines.

6 Claims, 1 Drawing Figure

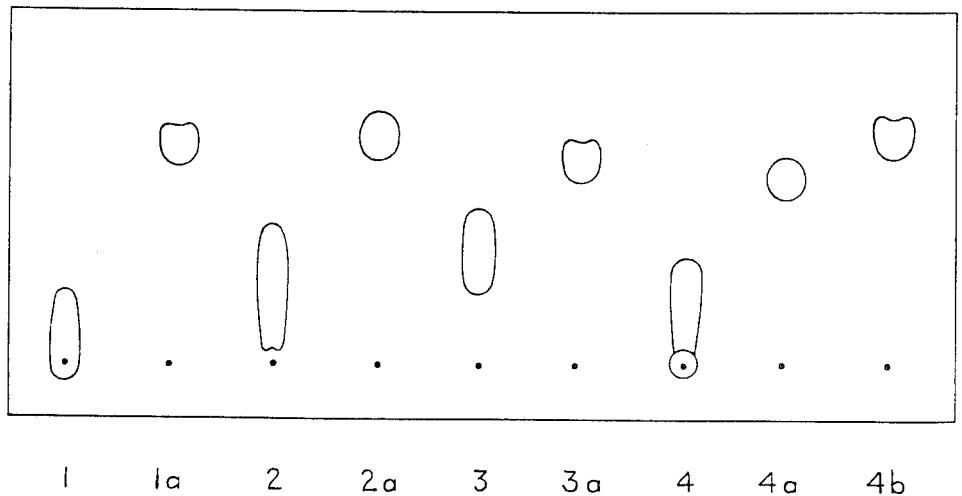

1 Amino methane diphosphonic acid
1a N-Propionyl amino methane diphosphonic acid (example 1)
2 1-Amino propane-1,1-diphosphonic acid
2a N-Acetyl-1-amino propane-1,1-diphosphonic acid (example 4)
3 N-Methylamino methane diphosphonic acid
3a N-Acetyl-N-methylamino methane diphosphonic acid (example 3)
4 1-Amino ethane-1,1-diphosphonic acid
4a N-Acetyl-1-amino ethane-1,1-diphosphonic acid (example 6)
4b N-Propionyl-1-amino ethane-1,1-diphosphonic acid (example 2)

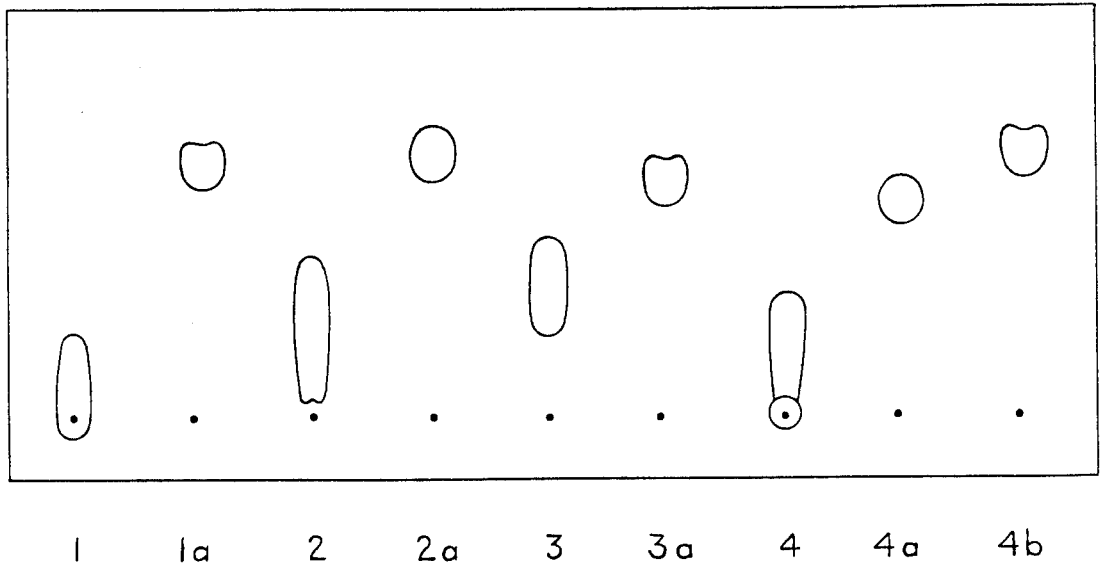

1 Amino methane diphosphonic acid
1a N-Propionyl amino methane diphosphonic acid (example 1)
2 1-Amino propane-1,1-diphosphonic acid
2a N-Acetyl-1-amino propane-1,1-diphosphonic acid (example 4)
3 N-Methylamino methane diphosphonic acid
3a N-Acetyl-N-methylamino methane diphosphonic acid (example 3)
4 1-Amino ethane-1,1-diphosphonic acid
4a N-Acetyl-1-amino ethane-1,1-diphosphonic acid (example 6)
4b N-Propionyl-1-amino ethane-1,1-diphosphonic acid (example 2)

N-ACYL-1-AMINO ALKANE-1,1-DIPHOSPHONIC ACID COMPOUNDS AND COMPOSITIONS FOR AND METHOD OF USING SAME

This is a division of application Ser. No. 677,286, filed Apr. 15, 1976, now U.S. Pat. No. 4,029,697.

BACKGROUND OF THE INVENTION

(1) Field of the Invention

The present invention relates to novel alkane diphosphonic acids and more particularly to novel N-acylated amino alkane diphosphonic acids, to methods of using same for their sequestering and scale formation preventing effect, and to compositions containing such compounds, said compositions being useful as scale formation preventing agents.

(2) Description of the Prior Art

The most important representative of amino alkane phosphonic acids as they were known heretofore, is the 1-amino ethane-1,1-diphosphonic acid. Said phosphonic acid, however, has the disadvantage that it is difficultly soluble in water and also in alkaline solutions. Due to its low solubility, the 1-amino ethane-1,1-diphosphonic acid is unsuitable for many purposes.

1-amino alkane 1,1-diphosphonic acids which are substituted at the amino group, have also been produced heretofore. One or two hydrogen atoms of the amino group of such compounds have been replaced by alkyl, aralkyl, phenyl, or cycloaliphatic residues. Compounds of this type are, for instance, N-methyl- or N,N-dimethyl-1-amino ethane-1,1-diphosphonic acids. But said acids are also difficultly soluble like the 1-amino ethane-1,1-diphosphonic acid.

SUMMARY OF THE INVENTION

It is one object of the present invention to provide new and highly advantageous amino alkane phosphonic acid compounds, namely N-acyl-1-amino alkane-1,1-diphosphonic acids.

A further object of the present invention is to provide compositions containing said N-acyl-1-amino alkane-1,1-diphosphonic acids. Said compositions are useful for preventing deposition of scale forming precipitates in aqueous systems.

A further object of the present invention is to provide novel and highly effective detergent and cleaning compositions containing such N-acyl-1-amino alkane-1,1-diphosphonic acids. Said compositions can especially be used as additives to cleaning solutions for bottle rinsing machines and in tank and container cleaning operations.

A further object of the present invention is to provide a method of using such N-acyl-1-amino alkane-1,1-diphosphonic acids in order to prevent scale and deposit formation in aqueous systems, to inhibit corrosion, and to exert a sequestering and complex-forming effect with respect to bivalent and polyvalent metal ions.

Other objects of the present invention will become apparent as the description proceeds.

In principle, the novel phosphonic acid compounds according to the present invention are N-acyl-1-amino alkane-1,1-diphosphonic acid compounds of the following formula:

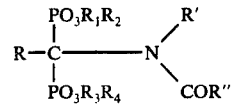

In said formula
R, R', and R" indicate hydrogen or lower alkyl, preferably methyl, ethyl, or propyl;
while
$R_1$, $R_2$, $R_3$ and $R_4$ indicate hydrogen or an alkali metal, preferably sodium.

The new compounds have an excellent scale and deposit formation preventing and sequestering effect which is far superior to the effect caused by the known phosphonic acids which are not acylated at the amino group. In addition thereto, the compounds according to the present invention are readily soluble in water. Their high solubility in water is of very considerable importance for their use as scale formation preventing and sequestering agents in aqueous systems. Thus they can be used in many instances in which the corresponding non-acylated phosphonic acids could not be employed.

The acylated amino alkane phosphonic acid compounds according to the present invention can be prepared in a simple manner by acylating the alkali metal salts of the corresponding 1-amino alkane-1,1-diphosphonic acids.

Suitable acylating agents are the acid anhydrides or acid chlorides of lower alkanoic acids or formic acid.

For producing the compounds of the present invention preferably the phosphonic acid salt and the acylating agent are mixed with each other. The resulting mixture is heated under reflux while stirring at the same time. The salt of the phosphonic acid can be added in solid form. It is, however, also possible to produce the salt in the reaction mixture by the addition of an alkali metal hydroxide solution and then to acylate the resulting reaction mixture without isolating the alkali metal salt.

The progress of the acylation reaction can be ascertained by means of a thin layer chromatogram, since the acylation products are very considerably distinguished in their RF-values (retardation factor values) over the starting materials. When proceeding in this manner, a reaction solution is obtained from which the reaction product is recovered in solid form by evaporation to dryness in a vacuum or by precipitation with a suitable water-miscible solvent, such as an alcohol, for instance, n-butanol or propanol-(2); glacial acetic acid, acetone; and others. It is also possible to use the acylation solution directly without first isolating the reaction product.

If desired, the salts of the phosphonic acids can be converted in a manner known per se into the free acids, for instance, by neutralization or by a treatment with an ion exchange agent.

The N-acyl-1-amino alkane-1,1-diphosphonic acids and their alkali metal salts can also be produced by alkaline hydrolysis of N-(1,1-diphosphono alkane) acylamidines, for instance, of N-(1,1-diphosphono ethyl) acetamidine which yields the N-acetyl-1-amino ethyl-1,1-diphosphonic acid, or of N-(diphosphono methyl) formamidine which yields the N-formylamino methane diphosphonic acid.

The N-acyl-1-amino alkane-1,1-diphosphonic acids according to the present invention or, respectively, their alkali metal salts are capable of preventing deposition of scale forming deposits in aqueous systems even when added thereto in substoichiometrical amounts (seeding amounts). In addition thereto the novel phosphonic acid compounds have an excellent complexing power with respect to bivalent and polyvalent metal ions, for instance, with respect to calcium, magnesium, iron, chromium, manganese, and other ions. They also exert a high corrosion inhibiting effect. They can be incorporated into solid or liquid preparations to be used in aqueous media. The new phosphonic acids are also well compatible with the conventional washing and cleaning agents and detergents as they are added to and used in aqueous media. Thus, they can be combined with conventional washing and cleaning agents and detergents to yield scale formation preventing washing and detergent compositions. Their addition, for instance, to washing and cleaning agents used in automatically operating bottle rinsing machines or in the cleaning of tanks and containers has proved to be especially valuable.

The following Table 1 illustrates the surprisingly improved scale formation preventing effect of the N-acyl-1-amino alkane-1,1-diphosphonic acids according to the present invention in comparison to the corresponding non-acylated 1-amino alkane-1,1-diphosphonic acids at an alkaline pH-value of the aqueous medium while Table 2 shows said effect in an aqueous medium of a pH of 7.0. In said Tables the sodium salts of the phosphonic acids obtained according to the examples were calculated as free phosphonic acids.

TABLE 1.

| Compound | mg. | Threshold effect at an alkaline pH-value of the aqueous medium Seeding effect, i.e. calcite | | | | | | | | | |
|---|---|---|---|---|---|---|---|---|---|---|---|
| | | 1 | 2 | 3 | 4 | 5 | 6 | 7 | 8 | 9 | 10 |
| N-Propionylamino meth- and diphosphonic acid (Example 1) | 3 | 0 | — | — | — | — | — | — | — | — | — |
| | 5 | 0 | 0 | 0 | — | — | — | — | — | — | — |
| | 10 | 0 | 0 | 0 | 0 | 0 | | | | | |
| Amino methane- diphosphonic acid | 3 | — | — | — | — | — | — | — | — | — | — |
| | 5 | — | — | — | — | — | — | — | — | — | — |
| | 10 | 0 | — | — | — | — | — | — | — | — | — |
| N-Acetyl-N-methylamino methane) diphos- (Example 3) | 3 | 0 | — | — | — | — | — | — | — | — | — |
| | 5 | 0 | 0 | 0 | 0 | — | — | — | — | — | — |
| | 10 | 0 | 0 | 0 | 0 | 0 | 0 | 0 | — | — | — |
| N-Methylamino methane- diphosphonic acid | 3 | — | — | — | — | — | — | — | — | — | — |
| | 5 | 0 | — | — | — | — | — | — | — | — | — |
| | 10 | 0 | 0 | 0 | — | — | — | — | — | — | — |
| N-Acetyl-1-amino ethane- 1,1-diphosphonic acid (Example 6) | 3 | 0 | 0 | 0 | 0 | 0 | 0 | — | — | — | — |
| | 5 | 0 | 0 | 0 | 0 | 0 | 0 | 0 | 0 | 0 | 0 |
| N-Propionyl-1-amino ethane-1,1-diphosphonic acid (Example 2) | 3 | 0 | 0 | — | — | — | — | — | — | — | — |
| | 5 | 0 | 0 | 0 | 0 | 0 | 0 | 0 | — | — | — |
| 1-Amino ethane-1,1-di- phosphonic acid | 3 | 0 | — | — | — | — | — | — | — | — | — |
| | 5 | 0 | 0 | 0 | 0 | — | — | — | — | — | — |
| N-Acetyl-1-amino pro- pane-1,1-diphosphonic acid (Example 4) | 3 | 0 | 0 | — | — | — | — | — | — | — | — |
| | 5 | 0 | 0 | 0 | 0 | 0 | — | — | — | — | — |
| 1-Amino propane-1,1- diphosphonic acid | 3 | 0 | — | — | — | — | — | — | — | — | — |
| | 5 | 0 | 0 | 0 | 0 | — | — | — | — | — | — |

In said Table
   0 indicates that no crystals, i.e. incrustations are deposited on the glass rod and/or the wall of the beaker, while
   - indicates calcite precipitation.

In order to determine the threshold or seeding value as shown in Table 1, there was dissolved a pre-determined amount, in mg., of the compound to be tested in a glass beaker in one liter of water of 18.9° German hardness to which 12 g. of sodium hydroxide were added. The glass beaker was covered with a watch glass and was allowed to stand at room temperature. It was then observed and noted after how many days a glass rod placed into the beaker and/or the walls of the beaker showed formation and deposition of crystals thereon. The pH-value of the alkaline asolution was 11.0.

TABLE 2

| Threshold effect at a pH of 7.0 and 80° C. | |
|---|---|
| Compound | m val. of alkaline earth metal ions |
| N-Propionylamino methane diphosphonic acid (Example 1) | 4.86 |
| Amino methane diphosphonic acid | 2.79 |
| N-acetyl-N-methylamino methane diphosphonic acid (Example 3) | 5.25 |
| N-Methylamino methane diphosphonic acid | 4.46 |
| N-Propionyl-1-amino methane-1,1-diphosphonic acid (Example 2) | 4.54 |
| 1-Amino ethane-1,1-diphosphonic acid | 3.97 |
| N-Acetyl-1-amino propane-1,1-diphosphonic acid (Example 4) | 5.25 |
| 1-Amino propane-1,1-diphosphonic acid | 5.04 |

To determine the effect of the acylated amino alkane-1,1-diphosphonic acid compounds according to the present invention at a pH of 7.0, 2.0 mg. of the compound to be tested, calculated as free acid, were added to 100 cc. of water of a known hardness. The solution was adjusted to a pH of 7.0 and was kept in a warming cabinet at 80° C. for 16 hours. The aqueous solution was then filled up with distilled water to 100 cc., filtered through a double-folded filter, and the residual hardness was determined in the filtrate and calculated as m val. of alkaline earth metal ions according to the DIN 19 640 specifications. 1 m val. of alkaline earth metal ions corresponds to 2.8° German hardness.

The following Table 3 shows the sequestering or complex-binding capacity of the N-acylated amino alkane-1,1-diphosphonic acid according to the present invention with respect to calcium ions.

TABLE 3

| Compounds | cc. of 0.25 molar calcium acetate solution | mg. of calcium carbonate per g. of compound | Mol. of calcium per mol. of compound |
| --- | --- | --- | --- |
| N-Propionylamino methane diphosphonic acid (Example 1) | 60.6 | 1,515.0 | 2.90 |
| N-Formylamino methane diphosphonic acid (Example 7) | 37.5 | 936.0 | 2.02 |
| Amino methane diphosphonic acid | 24.5 | 612.5 | 1.17 |
| N-Acetyl-N-methylamino methane diphosphonic acid (Example 3) | 87.0 | 2,175.0 | 4.46 |
| N-Methylamino methane diphosphonic acid | 45.6 | 1,140.0 | 2.34 |
| N-Acetyl-1-amino ethane-1,1-diphosphonic acid (Example 6) | 55.0 | 1,375.0 | 4.06 |
| N-Propionyl-1-amino ethane-1,1-diphosphonic acid (Example 2) | 65.1 | 1,627.5 | 3.34 |
| 1-Amino ethane-1,1-diphosphonic acid | 49.6 | 1,240.0 | 2.54 |
| N-Acetyl-1-amino propane-1,1-diphosphonic acid (Example 4) | 100.4 | 2,510.0 | 5.50 |
| 1-Amino propane-1,1-diphosphonic acid | 57.8 | 1,445.0 | 3.17 |

In order to determine the sequestering capacity with respect to calcium ions as given in Table 3 there were dissolved 1 g. of the compound to be tested in 70 cc. of distilled water. The pH-value of said solution was adjusted to a pH of 11.5 by the addition of N sodium hydroxide solution while stirring. 10 cc. of a 2% sodium carbonate solution were added to the clear solution, whereafter an 0.25 molar calcium acetate solution was added drop by drop thereto until the solution remained permanently turbid so that the numbers or letters of a card placed behind the glass beaker could no more be deciphered.

BRIEF DESCRIPTION OF THE DRAWING

The attached drawing illustrates the thin layer chromatograms of N-acylated amino alkane-1,1-diphosphonic acids according to the present invention in comparison with the thin layer chromatograms of the corresponding non-acylated amino alkane-1,1-diphosphonic acids.

DESCRIPTION OF THE PREFERRED EMBODIMENTS

The following examples serve to illustrate the present invention without, however, being limited thereto.

Example 1

19.1 g. (0.1 mole) of amino methane diphosphonic acid are dissolved in 9 cc. (0.5 moles) of water and 12 g. (0.3 moles) of sodium hydroxide. 130.14 g. (1 mole) of propionic acid anhydride are added thereto and the mixture is boiled for 3 hours to 4 hours while slightly refluxing. N-propionylamino methane diphosphonic acid is obtained in solution.

The progress of the acylation reaction can be followed by means of a thin-layer chromatogram. The N-acyl compound has a smaller RF-value than the non-acylated phosphonic acid. Developing solvent: 350 cc. of propanol-(2), 50 cc. of water, 20 g. of trichloro acetic acid dissolved in 80 cc. of water, and 0.5 cc. of concentrated ammonia.

In order to isolate the N-propionylamino methane diphosphonic acid, the reaction solution is concentrated by evaporation in a vacuum. The resulting partly crystallizing heavy sirup is triturated with 60 cc. of n-butanol and the pure white precipitate is filtered off by suction. After drying, 28.4 g. (90.8% of the theoretical yield) of the trisodium salt of N-propionylamino methane diphosphonic acid are obtained.

Analysis:

| Calculated: | 4.47 % N; | 19.8 % P; | 22.05 % Na. |
| --- | --- | --- | --- |
| Found: | 4.60 % N; | 19.5 % P; | 21.00 % Na. |

The drawing shows the thin-layer chromatogram of N-propionylamino methane diphosphonic acid (1a) compared with that of the starting amino methane diphosphonic acid (1).

Example 2

20.5 g. (0.1 mole) of 1-amino ethane-1,1-diphosphonic acid are added to a cold sodium hydroxide solution of 18 g. of water and 4 g. of sodium hydroxide, while stirring. A solution of the mono-sodium salt of said acid is obtained which remains clear for 2 to 3 seconds. Said solution solidifies immediately to a paste similar to a polymer. The resulting almost solid mass is then introduced into 169.2 g. (1.3 moles) of propionic acid anhydride. The mixture is boiled under reflux for 3 to 4 hours and is filtered. The filtrate contains the monosodium salt of N-propionyl-1-amino ethane-1,1-diphosphonic acid. The progress of the acylation reaction can be observed by means of a thin-layer chromatogram. The N-acyl compound has a smaller RF-value than the non-acylated phosphonic acid.

In order to produce the crystalline compound, the resulting solution is cooled to 10° C. Thereby the crystalline salt of the phosphonic acid is obtained.

Analysis:

| Calculated: | 4.95 % N; | 21.9 % P; | 8.1 % Na. |
| --- | --- | --- | --- |
| Found: | 5.25 % N; | 23.0 % P; | 8.2 % Na. |

The drawing shows the thin-layer chromatogram of N-propionyl-1-amino ethane-1,1-diphosphonic acid (4b) compared with that of the starting 1-amino ethane-1,1-diphosphonic acid (4).

Example 3

24.9 g. (0.1 mole) of the disodium salt of N-methylamino methane diphosphonic acid are boiled under reflux in 51 g. (0.5 moles) of acetic acid anhydride for 2 hours. The clear solution containing about 40 % of the reaction product can be used as such.

In order to produce the solid phosphonic acid salt, the solution is concentrated by evaporation in a vacuum in a boiling water bath. The residue is pulverized, boiled briefly in 200 cc. of ethanol, filtered off by suction, and dried at 130° C. in a vacuum overnight. Yield: 27.6 g. of the di-sodium salt of N-acetyl-N-methylamino methane diphosphonic acid, corresponding to 95.0% of the theoretical yield are obtained.

| Analysis: | | | |
| --- | --- | --- | --- |
| Calculated: | 4.8 % N; | 21.3 % P; | 15.8 % Na |
| Found: | 5.2 % N; | 21.8 % P; | 15.2 % Na |

The drawing shows the thin-layer chromatogram of N-acetyl-N-methylamino methane diphosphonic acid (3a) compared with that of the starting N-methylamino methane diphosphonic acid (3).

Example 4

21.9 g. (0.1 mole) of 1-amino propane-1,1-diphosphonic acid are added to a cold solution of 81.7 g. (0.8 moles) of acetic acid anhydride and 13 g. of dilute sodium hydroxide solution (4 g. of sodium hydroxide in 9 g. of water). The mixture is heated while stirring and is boiled under reflux for 3 to 4 hours. The resulting solution is concentrated by evaporation in a vacuum, the residue is pulverized, suspended in alcohol, and dried. Yield: 24.9 g. of the monosodium salt of N-acetyl-1-amino propane-1,1-diphosphonic acid corresponding to 88 % of the theoretical yield.

| Analysis: | | | |
| --- | --- | --- | --- |
| Calculated: | 4.95 % N; | 21.9 % P; | 8.1 % Na. |
| Found: | 5.10 % N; | 21.5 % P; | 9.1 % Na. |

The drawing shows the thin-layer chromatogram of N-acetyl-1-amino propane-1,1-diphosphonic acid (2a) compared with that of the starting 1-amino propane-1,1-diphosphonic acid (2).

Example 5

20.5 g. (0.1 mole) of N-methylamino methane-diphosphonic acid are suspended in a dilute sodium hydroxide solution (4 g. (0.1 mole) of sodium hydroxide in 9 cc. of water). 46.03 g. (1 mole) of formic acid are added to said solution. The mixture is then heated to boiling. As soon as it has attained reflux temperature, a clear solution is formed. The reaction is completed after 2½ hours. The solution is then added drop by drop to 400 cc. of acetone while stirring. After filtering by suction and drying of the pure white precipitate, 23.9 g. of the monosodium salt of N-formyl-N-methylamino methane diphosphonic acid, corresponding to 93.7% of the theoretical yield, are obtained.

| Analysis: | | | |
| --- | --- | --- | --- |
| Calculated: | 5.5 % N; | 24.3 % P; | 11.1 % Na; |
| Found: | 5.9 % N; | 24.1 % P; | 10.5 % Na. |

Example 6

22.7 g. (0.1 mole) of the mono-sodium salt of 1-amino ethane-1,1-diphosphonic acid are boiled under reflux in 30.6 g. (0.3 moles) of acetic acid anhydride for about 30 minutes. A clear solution is obtained. On cooling, a viscous yellowish sirup is produced. The sirup can be diluted with water and the aqueous solution can be used directly. In order to recover the crystalline reaction product, the sirup is added with stirring to 40 cc. of glacial acetic acid and the resulting crystalline product is filtered off by suction. After drying, 20.3 g. of the mono-sodium salt of N-acetyl-1-amino ethane-1,1-diphosphonic acid, corresponding to 75.4% of the theoretical yield, are obtained.

| Analysis: | | | |
| --- | --- | --- | --- |
| Calculated: | 5.2 % N; | 23.1 % P; | 8.55 % Na. |
| Found: | 5.3 % N; | 24.0 % P; | 9.30 % Na. |

Progress of the acylation can be observed by thin-layer chromatography. The N-acyl compound has a smaller RF-value than the non-acylated phosphonic acid. See the thin-layer chromatogram of N-acetyl-1-amino ethane-1,1-diphosphonic acid (4a) of the drawing compare with that of the starting 1-amino ethane-1,1-diphosphonic acid (4).

Example 7

19.1 g. (0.1 mole) of amino methane diphosphonic acid are dissolved in 9 cc. of water and 4 g. (0.1 mole) of sodium hydroxide. 46.03 g. (1.0 mole) of formic acid are added thereto. The mixture is boiled for 1 to 2 hours while slightly refluxing the same. Thereupon, the clear solution is added drop by drop to about 500 cc. of methanol while stirring. 21.3 g. of the mono-sodium salt of N-formylamino methane diphosphonic acid, corresponding to 88.5% of the theoretical yield, are obtained.

| Analysis: | | | |
| --- | --- | --- | --- |
| Calculated: | 5.8 % N; | 26.1 % P; | 9.5 % Na. |
| Found: | 6.1 % N; | 25.8 % P; | 10.0 % Na. |

Example 8

A solution of 24.6 g. (0.1 mole) of N-(1,1-diphosphono ethyl) acetamidine in a sodium hydroxide solution prepared from 250 cc. of water and 28.0 g. (0.7 moles) of sodium hydroxide, is heated under reflux for 30 minutes, cooled somewhat, and poured into 1.5 liters of methanol. The resulting precipitate which is very readily soluble in water is filtered off by suction. Yield: 38.3 g.

In order to purify the crude reaction product, it is suspended in about 75 cc. of water. Concentrated hydrochloric acid is added to the suspension until a pH of 1.0 to 2.0 is attained. Thereafter, the solution is boiled for a short period of time, treated with animal charcoal, and filtered while still hot. 30 cc. of methanol are added to the hot filtrate. Thereby the solution becomes turbid and finally crystallizes through and through. The crystalline product is filtered off by suction and is washed with a small amount of water and methanol. After drying at 130° C. the mono-sodium salt of N-acetyl-1-amino ethane-1,1-diphosphonic acid is obtained. Yield: 26.8 g. (theoretical yield: 26.9 g.) Melting point: 275° C. with decomposition.

| Analysis: | | | |
|---|---|---|---|
| Calculated: | 5.2 % N; | 23.0 % P; | 8.5 % Na. |
| Found: | 5.5 % N; | 22.8 % P; | 7.5 % Na. |

The presence of the N-acetyl group was demonstrated by the proton nuclear magnetic resonance spectrum.

Example 9

A solution of 21.8 g. (0.1 mole) of N-(diphosphono methyl) formamidine in a sodium hydroxide solution prepared by dissolving 16.0 g. (0.4 moles) of sodium hydroxide in 250 cc. of water, is heated under reflux for about 15 minutes. The solution can be used as such without isolating the compound according to the present invention.

To isolate said compound, the reaction solution is poured into 1.5 liters of methanol. The resulting precipitate is filtered off by suction and is dried. Yield: 22.9 g. of the tetra-sodium salt of N-formylamino methane diphosphonic acid (theoretical yield:32.6 g.)

| Analysis: | | | | |
|---|---|---|---|---|
| Calculated: | 4.3 % N; | 19.1 % P; | 28.2 % Na; | 5.5 % H$_2$O. |
| Found: | 4.4 % N; | 20.0 % P; | 25.1 % Na; | 4.4 % H$_2$O. |

The N-(1,1-diphosphono alkane) acylamidines used in Examples 8 and 9 as starting materials can be prepared in a manner known per se, for instance, as described in U.S. Pat. No. 3,919,297 and in German Published Application No. 2,439,355.

In general the novel N-acyl-1-amino alkane-1,1-diphosphonic acids according to the present invention are prepared either (a) by hydrolyzing an N-(1,1-diphosphono alkane) acylamidine of the following Formula II

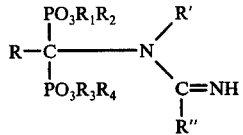

in which

R and R" are hydrogen or lower alkyl;
R' is lower alkyl; and
R$_1$, R$_2$, R$_3$, and R$_4$ are hydrogen or an alkali metal,
or (b) by hydrolyzing an N-(1,1-diphosphono alkane) acylamidine of the following Formula III:

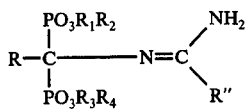

in which

R and R" are hydrogen or lower alkyl; and
R$_1$, R$_2$, R$_3$, and R$_4$ are hydrogen or an alkali metal.

Hydrolysis is effected in both instances in the presence of an alkali metal hydroxide.

When carrying out hydrolysis with the acylamidine of Formula III, the substituent R' in the resulting diphosphonic acid is hydrogen while when hydrolyzing the acylamidine of Formula II, said substituent is lower alkyl.

The following Table 4 shows the improved threshold or seeding effect of N-acetyl-1-amino ethane-1,1-diphosphonic acid (AADP) according to the present invention compared with that of the known phosphonic acid acetamidine, namely N-(1,1-diphosphono ethyl) acetamidine (DPAA), with 1-amino ethane-1,1-diphosphonic acid (ADP), and with 1-hydroxy ethane-1,1-diphosphonic acid (HDP). While the N-(1,1-diphosphono alkane) acetamidine has a certain threshold or seeding effect, this effect is considerably improved by hydrolyzing said acetamidine compounds to the corresponding N-acetyl-1-amino alkane-1,1-diphosphonic acids according to the present invention.

Furthermore, the complexing or sequestering power of the compounds according to the present invention is also considerably increased over that of the corresponding acylamidine compounds.

TABLE 4

| | | Threshold effect at an alkaline pH-value of the aqueous medium | | | | | | | | | | |
|---|---|---|---|---|---|---|---|---|---|---|---|---|
| | | Seeding effect, i.e. calcite crystals deposited after days | | | | | | | | | | |
| Compound | Amount mg. | 1 | 2 | 3 | 4 | 5 | 6 | 7 | 8 | 9 | 10 | 11 |
| AADP | 3 | 0 | 0 | 0 | 0 | 0 | 0 | — | — | — | — | — |
| | 5 | 0 | 0 | 0 | 0 | 0 | 0 | 0 | 0 | 0 | 0 | 0 |
| DPAA | 3 | 0 | 0 | 0 | 0 | 0 | — | — | — | — | — | — |
| | 5 | 0 | 0 | 0 | 0 | 0 | 0 | 0 | 0 | — | — | — |
| ADP | 3 | 0 | 0 | — | — | — | — | — | — | — | — | — |
| | 5 | 0 | 0 | 0 | 0 | 0 | — | — | — | — | — | — |
| HDP | 3 | — | — | — | — | — | — | — | — | — | — | — |
| | 5 | 0 | 0 | — | — | — | — | — | — | — | — | — |

In said Table 0 indicates that no crystals, i.e. incrustations are deposited on the glass rod and/or the wall of the beaker, while

- indicates calcite precipitation.

The threshold or seeding effect is determined in the same manner as described in Table 1 whereby a water of a degree of German hardness of 17.9° is used.

The following Table 5 illustrates the tests showing the complexing or sequestering power with respect to calcium ions of the compounds according to the present invention compared with other known phosphonic acid compounds, namely of N-acetyl-1-amino ethane-1,1-diphosphonic acid (AADP) according to the present invention compared with N-(1,1-diphosphono ethyl) acetamidine (DPAA) and 1-amino ethane-1,1-diphosphonic acid (ADP) and of N-formylamino methyl diphosphonic acid according to the present invention (FADP) compared with N-(diphosphono methyl) formamidine (DPFA) and amino methane diphosphonic acid (AMDP).

TABLE 5

| Compounds | cc. of 0.25 molar calcium acetate solution | mg. of calcium carbonate per g. of compound | Mol. of calcium per mol. of compound |
|---|---|---|---|
| AADP | 55.0 | 1,375 | 4.06 |
| DPAA | 54.6 | 1,365 | 3.36 |
| ADP | 49.6 | 1,240 | 2.54 |

TABLE 5-continued

| Compounds | cc. of 0.25 molar calcium acetate solution | mg. of calcium carbonate per g. of compound | Mol. of calcium per mol. of compound |
|---|---|---|---|
| FADP | 37.5 | 936 | 2.02 |
| DPFA | 24.5 | 612 | 1.33 |
| AMDP | 22.5 | 563 | 1.08 |

Determination of the sequestering power is carried out in the same manner as described with respect to Table 3.

The following Table 6 shows the complexing or sequestering power with respect to magnesium ions and the following Table 7 that with respect to ferric ions. In said Tables 6 and 7 there are compared N-acetyl-N-methylamino methane diphosphonic acid of Example 3 with the starting N-methylamino methane diphosphonic acid.

TABLE 6

| Compound | mg. Mg. by each g. of compound | mole Mg by each mole of compound |
|---|---|---|
| N-Methylamino methane diphosphonic acid | 333 | 2.81 |
| N-Acetyl-N-methylamino methane diphosphonic acid | 634 | 6.44 |

Determination of the sequestering power is carried out in the same manner as described with respect to Table 3 whereby, however, an 0.25 molar magnesium acetate solution is used in place of the 0.25 molar calcium acetate solution.

TABLE 7

| Compound | mg. Fe(III) for each 100 mg. of compound | g.-Atoms of Fe(III) for each mole of compound |
|---|---|---|
| N-Methylamino methane diphosphonic acid | 26.3 | 0.96 |
| N-Acetyl-N-methylamino methane diphosphonic acid | 35.2 | 1.50 |

The sequestering power with respect to ferric ions was determined according to the thiocyanate method at a pH of about 2.0 to 2.5. According to said method 100 mg. of the compound to be tested were dissolved in 50 cc. of distilled water in a 100 cc. glass beaker while stirring by means of a magnetic stirring device. 1 cc. of 0.1 N hydrochloric acid and 1 cc. of an 0.1 N ammonium thiocyanate solution are added thereto and the resulting solution is titrated, while stirring continuously, by the addition of an 0.1 molar ferric chloride solution until the solution attains a permanent pink coloration.

The N-acylamino alkane diphosphonic acid compounds according to the present invention are added to conventional cleaning compositions and especially to acid or alkaline cleaning or rinsing fluids. Improved cleaning or rinsing fluids according to the present invention are, for instance, of the following composition without, however, being limited thereto.

Example 10

| Composition: | |
|---|---|
| Mixture of phosphoric acid mono- and dimethyl esters (Knapsack A.G.) | 40 % |
| N-acetyl-1-amino ethane-1,1-diphosphonic acid | 20 % |
| Antifoaming agent, i.e. a bulk polymer of ethylene oxide with polypropylene glycol sold under the trademark PLURONIC L 61 (Wyandotte) | 10 % |
| Water | 30 % |

0.2% of said composition are dissolved in a cleaning fluid consisting of an aqueous 1% sodium hydroxide solution. The resulting cleaning fluid has proved to be highly effective in the cleaning and rinsing of glass bottles.

Example 11

| Composition: | |
|---|---|
| Sodium silicate | 35 % |
| N-Formylamino methane diphosphonic acid | 3 % |
| Sodium carbonate | 20 % |
| Sodium hydroxide | 17 % |
| Wetting agent, the nonyl phenol polyglycol ether with 6 moles of ethylene oxide per mole of nonyl phenol sold under the trademark ARKOPAL N/O 60 (Hoechst) | 5 % |
| Sodium sulfate | 10 % |
| Trisodium orthophosphate | 10 % |

1% aqueous solutions of said mixture are advantageously used for cleaning and rinsing milk cans.

Example 12

The composition is the same as given hereinabove in Example 11, whereby, however, the N-formylamino methane diphosphonic acid is replaced by N-formyl-N-methylamino methane diphosphonic acid.

0.2% of the resulting composition are dissolved in aqueous 1% sodium hydroxide solution to yield a highly advantageous bottle rinsing solution.

Example 13

The composition is the same as given hereinabove in Example 10, whereby, however, the N-acetyl-1-amino ethane-1,1-diphosphonic acid is replaced by N-propionylamino methane diphosphonic acid.

1% Aqueous solutions of said mixture have proved to be effective cleaning fluids for milk cans.

Example 14

| Sodium tripolyphosphate | 40 % |
|---|---|
| N-Acetyl-1-amino propane-1,1-diphosphonic acid | 10 % |
| Antifoaming agent PLURONIC L 61 (Wyandotte) | 5 % |
| Trisodium orthophosphate | 10 % |
| Sodium gluconate | 35 % |

0.2% of said mixture are dissolved in aqueous 1.5% sodium hydroxide solution. The resulting solution is a highly effective solution for cleaning bottles and especially bottles with aluminum accessories such as aluminum labels and/or aluminum caps.

Example 15

| Composition: | |
|---|---|
| Mixture of phosphoric acid mono methyl ester and of phosphoric acid iso- | |

-continued

| Composition: | |
|---|---|
| propyl ester (Knapsack A.G.) | 40 % |
| N-Acetyl-N-methylamino methane diphosphonic acid | 20 % |
| Water | 40 % |

0.2% of said mixture are dissolved in aqueous 1% sodium hydroxide solution. The resulting cleaning solution has proved to be a highly effective bottle rinsing fluid.

Example 16

| Composition: | |
|---|---|
| Aqueous 67% gluconic acid solution | 70 % |
| N-Propionyl-1-amino ethane-1,1-diphosphonic acid | 20 % |
| Water | 10 % |

0.2% of said mixture are dissolved in aqueous 1% sodium hydroxide solution. The resulting cleaning solution has proved to be a highly effective bottle rinsing fluid.

Example 17

| Composition: | |
|---|---|
| Sodium silicate | 35 % |
| N-Acetylamino methane diphosphonic acid | 3 % |
| Sodium carbonate | 20 % |
| Sodium hydroxide | 17 % |
| Wetting agent, i.e. the nonyl phenol polyglycol ether with 6 moles of ethylene oxide per mole of nonyl phenol sold under the trademark ARKOPAL N/O (Hoechst) | 5 % |
| Sodium sulfate | 10 % |
| Trisodium orthophosphate | 10 % |

1% aqueous solutions of said mixture are advantageously used for cleaning and rinsing milk cans.

We claim:

1. In a process of preventing scale and deposit formation in aqueous systems, the step which comprises adding to the aqueous system, as scale and deposit formation suppressing agent, an N-acyl-1-amino alkane-1,1-diphosphonic acid of the formula

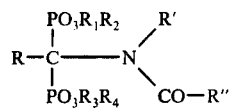

in which
R, R', and R" are hydrogen or lower alkyl and
$R_1$, $R_2$, $R_3$, and $R_4$ are hydrogen or an alkali metal, in substoichiometrical amounts calculated for the amount of hardness-causing compounds present in the aqueous system.

2. The process of claim 1, in which the N-acyl-1-amino alkane-1,1-diphosphonic acid compound is added to the aqueous system in an amount between about 3 mg./liter and about 300 mg./liter of the aqueous system.

3. In a process for sequestering in aqueous systems containing complex-forming metal ions, the step which comprises adding to the aqueous system an N-acyl-1-amino alkane-1,1-diphosphonic acid of the formula

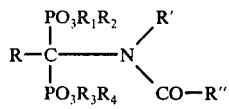

in which
R, R', and R" are hydrogen or lower alkyl and
$R_1$, $R_2$, $R_3$, and $R_4$ are hydrogen or an alkali metal.

4. A composition for suppressing scale and deposit formation in aqueous systems, said composition containing, as scale and deposit formation suppressing agent, an N-acyl-1-amino alkane-1,1-diphosphonic acid of the formula

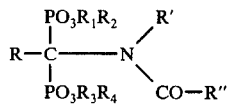

in which
R, R', R" are hydrogen or lower alkyl and
$R_1$, $R_2$, $R_3$, and $R_4$ are hydrogen or an alkali metal.

5. The composition as defined in claim 4 which is an aqueous fluid containing an amount of the scale and deposit formation suppressing agent of from about 3 mg/liter to about 300 mg/liter.

6. The composition as defined in claim 5 wherein the fluid further comprises a detergent agent.

* * * * *